United States Patent [19]
Schlatter et al.

[11] 4,113,713
[45] Sep. 12, 1978

[54] METHOD FOR CLEAVING THE PEPTIDE-RESIN BOND IN SOLID PHASE PEPTIDE SYNTHESIS BY HYDROGENOLYSIS

[75] Inventors: James M. Schlatter, Glenview; Owen Goodmonson, Chicago, both of Ill.

[73] Assignee: G. D. Searle & Co., Chicago, Ill.

[21] Appl. No.: 807,083

[22] Filed: Jun. 16, 1977

[51] Int. Cl.$^2$ .................. C07C 103/52; C07G 7/00
[52] U.S. Cl. .................. 260/112.5 R; 260/112.5 S; 260/112.5 LH; 260/112.5 T; 260/112.5 TR
[58] Field of Search ............... 260/112.5 S, 112.5 LH, 260/112.5 T, 112.5 R, 112.5 TR

[56] References Cited
PUBLICATIONS

B. W. Erickson and R. B. Merrifield, *The Proteins*, 3rd ed., vol. 11, (1976).
Res. Group Peptide Chem., Hung. Aeat. Sci. Hung. (C.A. 80 83584u).
R. B. Merrifield, *Advances in Enzymology*, 32, 1969, 221–295.
J. M. Stewart and J. D. Young, *Solid Phase Peptide Synthesis*, 1969.
Sugasaw et al., (C.A. 81 152637y).
C. Birr., Justus Leibigs, (C.A. 80 48385h).

*Primary Examiner*—Delbert R. Phillips
*Assistant Examiner*—Blondel Hazel
*Attorney, Agent, or Firm*—Michael T. Murphy

[57] ABSTRACT

An improved process for cleaving peptides bound to a polymer by way of a benzylester linkage during solid phase peptide synthesis, the improvement comprising hydrogenolysis of said linkage by catalytic hydrogenation using a palladium (II) salt with a weak acid anion as the catalyst.

2 Claims, No Drawings

METHOD FOR CLEAVING THE PEPTIDE-RESIN BOND IN SOLID PHASE PEPTIDE SYNTHESIS BY HYDROGENOLYSIS

SUMMARY OF INVENTION

The present invention relates to an improved process for cleaving peptides bound to a polymer by way of benzylester linkage during solid phase peptide synthesis, the improvement comprising hydrogenolysis of said linkage by catalytic hydrogenation using a palladium (II) salt with a weak acid anion as the catalyst.

DETAILED DESCRIPTION OF INVENTION

Solid-phase peptide synthesis is described in R.B. Merrifield, "Solid-Phase Peptide Synthesis," *Advances in Enzymology*, 32, 1969, 221-295, at page 223, as follows: "solid-phase peptide synthesis is based on the idea that a peptide chain can be assembled in a step-wise manner while it is attached at one end to a solid support. With the growing chain covalently anchored to an insoluble particle at all stages of the synthesis, the peptide will also be completely insoluble, and furthermore it will be a suitable physical form to permit rapid filtration and washing."

There are generally two types of resin supports used in solid-phase peptide synthesis, chloromethylated resin and benzhydrylamine resin. With the chloromethylated resin, the C-terminal amino acid is bound to the resin through an ester link as follows:

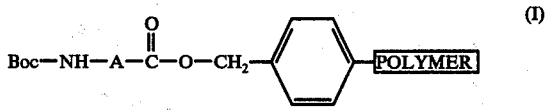

(I)

wherein Boc is a blocking group, in this case t-butyloxycarbonyl, and A represents the peptide, excluding the terminal amine and carboxyl groups. With the benzhydrylamine resin, the C-terminal amino acid is covalently bound to the amine group as follows:

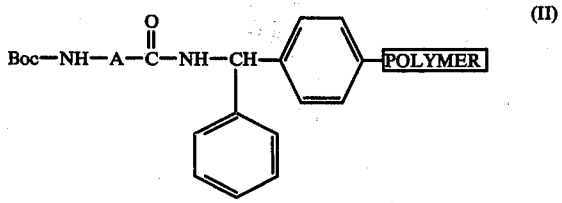

(II)

The process of the present invention is directed to the removal of peptides from resins which are bound through an ester link as shown in FIG. 1.

The typical procedure for cleaving the peptide from the resin has been to suspend the finished peptide-resin in anhydrous trifluoroacetic acid and bubble hydrogen bromide through the suspension. This reagent removes the t-butyloxycarbonyl protecting group by an elimination reaction, and cleaves the finished peptide from the resin by a nucleophilic displacement reaction. Also, certain other protecting groups used for amino acid side-chain functions are simultaneously removed from the peptide. J. M. Steward and J. D. Young, *Solid Phase Peptide Synthesis*, 1969 at page 2. Anhydrous liquid hydrogen fluoride is also used to cleave the peptide-resins, with similar results.

Hydrogenation has been used in deprotecting some finished peptides, but only after they have been removed from the resin. Typically, the nitro protecting group may be removed from nitroarginine and the benzyl protecting group may be removed from benzylhistidine by hydrogenation.

Published attempts to remove peptides from resins by catalytic hydrogenolysis have thus far failed. A recent article by B. W. Erickson and R. B. Merrifield in *The Proteins*, 3rd Edition, Vol. II, 1976, at page 386 states: "Cleavage of the benzylester link by catalytic hydrogenolysis has been attempted several times with uniformly poor results. Solid palladium and platinum catalysts are unable to penetrate the resin and make proper contact with the anchoring bond within the copoly-(styrenedivinylbenzene) beads. Attempts to deposit colloidal palladium in situ by reduction of a resin presoaked in a palladium chloride solution were also unsuccessful (R. B. Merrifield, unpublished observations)."

In the present invention, the finished peptide-resin is suspended in a solvent which swells the resin, and in which a catalyst which will penetrate the resin is soluble. Appropriate solvents are dimethylformamide, tetrahydrofuran and dioxane. These dipolar aprotic solvents swell resins used in solid phase synthesis and are stable to hydrogenation conditions. Protic solvents, such as lower alcohols and water, shrink the resin and reduce the hydrogenolysis.

Palladium and platinum salts which are soluble in the above solvents are catalysts which will penetrate the resin. Preferred catalysts are palladium salts having weak acid anions such as formate, acetate, propionate, butyrate and benzoate. A particularly preferred catalyst is palladium (II) acetate.

The mixture of peptide-resin, catalyst, and solvent is allowed to equilibrate. Then, the mixture is shaken with hydrogen, and hydrogen is taken up until cleavage is complete. The catalyst and resin are then removed by filtration and the solvent is distilled off under vacuum. The crude peptide can then be purified by any suitable procedure.

In addition to cleavage of the peptide-resin bond, the hydrogenation removes certain protecting groups as described above. An advantage of deprotection by hydrogenation is that the milder conditions involved in the removal prevents rearrangement of certain protected amino acids. When benzyltyrosine is present in the peptide, cleavage with hydrogen fluoride causes rearrangement of the benzyl tyrosine. When hydrogenation is used, the benzyl protecting group can be removed during the peptide-resin cleavage with no rearrangement.

An additional advantage of cleaving the peptide-resin by hydrogenolysis is that the t-butyloxycarbonyl blocking groups are not removed. A product obtained with these blocking groups intact may then be purified and used in further syntheses.

A number of variables to the hydrogenation conditions have been investigated. The pressure was changed from atmospheric to 500 psi with no apparent advantage to high pressure. The preferred pressure for most of the hydrogenations was 60 psi. Temperatures from ambient to 60° C were explored. A temperature of 40° C is preferred since it seems to increase the rate of hydrogenation and is less likely to cause decomposition of the product. Hydrogenations were run for times of 5 to 72 hours. 24 hours is adequate for most hydrogenations. If the yield of crude peptide is low, the resin can be rehydrogenated after the addition of more catalyst.

About 10 ml. of solvent is required for each gram of resin. The first 5 ml. is completely absorbed while the second 5 ml. permits adequate agitation. Under these conditions only half the catalyst actually diffuses into the resin. Molar ratios of palladium (II) acetate (the particularly preferred catalyst) to peptide substrate in the range of one to four have been tried; a ratio of two or three seems to work well. Thus, one molar equivalent of palladium is initially in contact with the peptide. Other catalyst failed completely; e.g. palladium black, $[(C_6H_5)_3P]_2PdCl_2$, $[(C_6H_5)_3P]_3RhCl$. The latter two are soluble in dimethylformamide but still liberated no peptide at all from the resin.

In order to illustrate the process of the present invention reference is made to the following examples, which are not intended to limit the invention in any respect. In the examples, the abbreviation Boc is used in its accepted meaning, referring to t-butyloxycarbonyl. The stereochemistry of each of the optically active amino acids in the examples is L unless otherwise indicated. Temperatures are given in degrees Centigrade (° C) and the relative amounts in parts by weight, except as otherwise noted.

EXAMPLE 1

One of the natural ligands for opitate receptors, leucine enkephalin having the formula H-Tyr-Gly-Gly-Phe-Leu-OH as described by Hughes, et. al., Nature 258, 577 (1975), was synthesized in the following manner:

The synthesis was performed with the aid of a Schwartz-Mann peptide synthesizer. The carboxyl-terminal amino acid, Boc-Leu, was attached to the chloromethylated, 1% cross-linked resin by the method of B. F. Gisin, Helv. Chem. Acta 56, 1476 (1973). The degree of substitution on the resin was 0.90 millimoles/g by Kjeldahl nitrogen analysis and the total weight of Boc-Leu-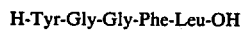was 14.6g. The scheme used for the preparation of Boc-Gly-Gly-Phe-Leu-®is shown in the table.

TABLE

| Step | Operation and Reagents | Time (min.) |
|---|---|---|
| 1 | Deblock-1; 40% TFA/CH$_2$Cl$_2$ | 40 |
| 2 | Washes; a. CH$_2$Cl$_2$ (3 times); b. i-PrOH (3 times); c. CH$_2$Cl$_2$ (5 times). | 1-1.5 each |
| 3 | Deblock-2; 40% TFA/CH$_2$Cl$_2$ | 30 |
| 4 | Washes; CH$_2$Cl$_2$ (5 times) | 1-1.5 each |
| 5 | Neutralization; 10% TFA/CH$_2$Cl$_2$ (4 times). | 1-1.5 |
| 6 | Washes; a. CH$_2$Cl$_2$ (3 times); b. i-PrOH (3 times); c. CH$_2$Cl$_2$ (7 times). | 1-1.5 each |
| 7 | Coupling; 2 equivalents of Boc-amino acid per equivalent of resin-bound peptide, 1 equivalent of DCC, CH$_2$Cl$_2$, symmetrical anhydride method. | 8 hr. |
| 8 | Washes; a. THF/CH$_3$OH (1:1) (3 times); b. CH$_2$Cl$_2$ (2 times); c. i-PrOH (3 times); d. CH$_2$Cl$_2$ (5 times). | 5 for THF/CH$_3$OH 1-1.5 each for others |
| 9 | Acetylation; 0.3M Ac$_2$O/CH$_2$Cl$_2$ (2 times) | 5 |
| 10 | Washes (as in Step 2). | |
| 11 | Repeat Steps 1-9. | |

Abreviations used: Boc — t-butyloxycarbonyl; DCC — dicyclohexylcarbodiimide; TFA — trifluoroacetic acid; TEA — triethylamine; ® — 1% cross-linked polystyrene resin bound to the aminoacid by a benzylester linkage; THF — tetrahydrofuran; Ac$_2$O — acetic anhydride; HOBt — 1-hydroxybenzotriazole; OPP — pentachlorophenoxy; DMF — dimethylformamide; HOAc — acetic acid. Other nomenclature from the IUPAC-IUB Commission on Biochemical Nomenclature, J. Biol. Chem. 241, 2491 (1966); 242, 555 (1967); 247, 977 (1972).

Deblocking was performed twice, with rather extended times to insure complete removal of the Boc group. Washes included a shrink-swell cycle with isopropyl alcohol as suggested by Marshall et. al., J. Org. Chem. 39, 44 (1974). The completion of each coupling step was determined with ninhydrin according to Kaiser et. al., Anal. Biochem. 34, 595 (1970), with acetylation of small amounts of free amino groups using acetic anhydride. Couplings were performed by means of the symmetrical anhydride, J. Rebeck and D. Feitler, J. Amer. Chem. Soc. 96, 1606 (1974), generated in the reactor. After four hours, more dicyclohexylcarbodiimide was added to regenerate additional anhydride. The final coupling utilized Boc-Tyr-OPP/HOBt in dimethylformamide as recently reported by Khan and Swanandaiah, Tetrahedron Letters, 199 (1976), although for 8 hours.

The removal of Box-Tyr-Gly-Gly-Phe-Leu-OH from the resin was accomplished by swelling the resin in a minimum amount of dimethylformamide in which was dissolved palladium (II) acetate (two equivalents per equivalent of peptide). After equilibration (about 2-2.5 hours), the peptide-resin was placed on a Parr shaker and hydrogenated at 60 psi, 40° C for 24 hours. Hydrogen uptake was initially very rapid as the palladium (II) acetate was reduced to palladium black in and around the beads. Total hydrogen uptake was about 20% over theory. The dimethylformamide containing the peptide was then removed from the resin-palladium black by filtration, and the beads were washed with dimethylformamide, then methylene chloride. The weight of the dried resins, minus the amount of palladium black formed, indicated essentially all of the peptide has been removed. Kjeldahal nitrogen analysis confirmed this, showing 0.09 millimoles/g. of material remaining.

The dimethylformamide was distilled from the peptide at 40° C under high vacuum. Trace amounts of dimethylformamide were then removed in a vacuum oven at 70° C for 4 hours to give an 87.8% crude yield of protected leucine enkaphalin. The product was purified by chromatography to afford a 56.4% yield of N-t-butyloxycarbonyl leucine enkaphalin.

Deblocking of the protected pentapeptide was performed by treating the blocked pentapeptide with hydrogen chloride in dioxane for 15 minutes at ambient temperature, evaporating the solvent at reduced pressure and crystallizing the final product with diethyl ether.

EXAMPLE 2

Boc-Tyr-Gly-Gly-Phe-Val-OH was prepared in the following manner: Boc-Tyr-Gly-Gly-Phe-Val- ® was prepared from Boc-Val-® (11.8 g., 0.86 millimole/g.). The resin was chloromethylated 1% cross-linked polystyrene in which about 90% of the chloromethyl groups were caused to react with Boc-Val. The coupling cycle was as described in Example 1 except that acetylation was omitted. A ninhydrin test was negative after each coupling. Boc-Tyr was attached via the pentachlorophenyl ester.

The peptide resin (5.3 g., 0.0035 mole based on weight gain) was added to a solution of 2.37 g. (0.0105 mole) of palladium (II) acetate in 55 ml. of dimethylformamide at 40° C. The mixture was shaken 15 minutes to swell the resin and diffuse the catalyst into it. The container was pressurized to 60 psi with hydrogen and shaken for 24 hours at 40° C. The solids were returned to a solution of 0.79 g. of palladium (II) acetate of dimethylformamide and hydrogenation repeated. The first run gave 1.99 g. of crude Boc-Tyr-Gly-Gly-Phe-Val and the second 0.39 g. The combined material was purified by partition chromatography on Sephadex LH-20 using the system chloroform:methanol:acetic acid:water (7:3:2:4) with a 4 × 55 cm column and a flow rate of 60 ml per hour. 20 ml fractions were collected. The desired product was eluted in fractions 96-146 to give 2.09 g of Boc-Tyr-Gly-Gly-Phe-Val as the monoacetate. The peptide was dissolved in 15 ml of methanol. 50 ml of water was then added and the mixture was taken to dryness under vacuum at 40° C. Two repetitions gave the compound free of acetic acid. The yield was 1.60 g.

What is claimed is:

1. In a process for cleaving peptides bound to a polymer by way of benzylester linkage during solid phase peptide synthesis, the improvement comprising hydrogenolysis of said linkage by catalytic hydrogenation using a palladium (II) salt with a weak acid anion as the catalyst.

2. In a process for cleaving peptides bound to a polymer by way of a benzylester linkage during phase peptide synthesis, the improvement comprising hydrogenolysis of said linkage by catalytic hydrogenation using palladium (II) acetate as the catalyst.

* * * * *